United States Patent
Linne et al.

(10) Patent No.: US 9,656,224 B2
(45) Date of Patent: May 23, 2017

(54) DYNAMIC MIXER

(75) Inventors: Volker Linne, Rosenthal-Roda (DE); Andreas Hiemer, Rebstein (CH); Florian Husler, Zug (CH)

(73) Assignee: SULZER MIXPAC AG, Haag (CH)

( * ) Notice: Subject to any disclaimer, the term of this patent is extended or adjusted under 35 U.S.C. 154(b) by 115 days.

(21) Appl. No.: 14/001,814

(22) PCT Filed: Feb. 9, 2012

(86) PCT No.: PCT/EP2012/052201
§ 371 (c)(1),
(2), (4) Date: Aug. 27, 2013

(87) PCT Pub. No.: WO2012/116883
PCT Pub. Date: Sep. 7, 2012

(65) Prior Publication Data
US 2013/0336083 A1    Dec. 19, 2013

(30) Foreign Application Priority Data
Feb. 28, 2011 (EP) .................................. 11156133

(51) Int. Cl.
*B01F 7/00* (2006.01)
*A61C 9/00* (2006.01)
(Continued)

(52) U.S. Cl.
CPC ........ *B01F 7/00233* (2013.01); *A61C 9/0026* (2013.01); *B01F 5/061* (2013.01);
(Continued)

(58) Field of Classification Search
CPC  B01F 7/0025; B01F 7/00258; B01F 7/00275; B01F 13/002; B01F 13/0022;
(Continued)

(56) References Cited

U.S. PATENT DOCUMENTS 3,293,117 A * 12/1966 Pennington, Jr. ... B01F 7/00641
162/236
3,293,118 A * 12/1966 Putnam ............... B01F 7/00641
137/859
(Continued)

FOREIGN PATENT DOCUMENTS

CN    201728077 U    2/2011
DE    199 47 331 A1   4/2001
(Continued)

OTHER PUBLICATIONS

International Search Report for International Patent Application No. PCT/EP2012/052201 mailed on Apr. 26, 2012.
(Continued)

*Primary Examiner* — Tony G Soohoo
*Assistant Examiner* — Elizabeth Insler
(74) *Attorney, Agent, or Firm* — Global IP Counselors, LLP (57) ABSTRACT

A dynamic mixer for a plurality of fluid components contains a housing and a rotor element which is rotatably arranged in the housing, with the housing having an inlet opening for at least one respective component and having at least one outlet opening. A ring-shaped intermediate space is provided between the rotor element and the housing in which a mixing element connected to the rotor element is arranged. The mixing element has a vane element which is formed as a directing element for conveying the components from the inlet opening to the outlet opening. The vane element is a directing element and has a directing surface which has a concave curvature with respect to the outlet opening and is further remote from the outlet opening at the onflow side than at the outflow side.

18 Claims, 6 Drawing Sheets

(51) Int. Cl.
*B01F 5/06* (2006.01)
*B01F 13/00* (2006.01)
*B01F 13/10* (2006.01)
*B05C 17/005* (2006.01)

(52) U.S. Cl.
CPC ...... *B01F 7/00125* (2013.01); *B01F 7/00141* (2013.01); *B01F 7/00216* (2013.01); *B01F 7/00258* (2013.01); *B01F 7/00275* (2013.01); *B01F 7/00291* (2013.01); *B01F 7/00641* (2013.01); *B01F 7/00775* (2013.01); *B01F 13/002* (2013.01); *B01F 13/103* (2013.01); *B01F 13/1027* (2013.01); *B05C 17/00566* (2013.01); *B01F 2005/0631* (2013.01); *B01F 2005/0636* (2013.01); *B01F 2215/0027* (2013.01); *B01F 2215/0039* (2013.01)

(58) Field of Classification Search
CPC .............. B01F 13/0023; B01F 13/0027; B01F 7/00641; B01F 7/0065; B01F 7/18; B01F 7/00708; B29C 47/667; B29C 47/60
USPC .................. 366/325.1, 325.2, 325.3, 325.92; D24/220, 221
See application file for complete search history.

(56) References Cited

U.S. PATENT DOCUMENTS

| | | | |
|---|---|---|---|
| 3,873,072 A * | 3/1975 | Blackmon | B01F 7/048 366/80 |
| 5,145,255 A * | 9/1992 | Shimada | B01F 7/0025 366/295 |
| 6,155,706 A | 12/2000 | Klein | |
| 6,523,992 B1 | 2/2003 | Bublewitz et al. | |
| 6,837,399 B1 | 1/2005 | Wagner et al. | |
| 7,230,037 B2 | 6/2007 | Sulzbach et al. | |
| 7,287,898 B2 | 10/2007 | Pauser et al. | |
| 7,674,033 B2 | 3/2010 | Pauser et al. | |
| 7,740,398 B2 * | 6/2010 | Cline | B01F 7/001 366/143 |
| 8,313,232 B2 | 11/2012 | Keller | |
| 2003/0107950 A1 | 6/2003 | Shepherd et al. | |
| 2004/0085854 A1 | 5/2004 | Pauser et al. | |
| 2004/0198870 A1 | 10/2004 | Sulzbach et al. | |
| 2008/0056061 A1 | 3/2008 | Pauser et al. | |
| 2008/0264809 A1 | 10/2008 | Knispel et al. | |
| 2009/0034357 A1 | 2/2009 | Gramann et al. | |
| 2009/0067284 A1 | 3/2009 | Wang | |
| 2009/0207685 A1 | 8/2009 | Busin et al. | |

FOREIGN PATENT DOCUMENTS

| | | |
|---|---|---|
| DE | 101 12 904 A1 | 10/2002 |
| DE | 102 42 100 A1 | 3/2004 |
| DE | 10 2007 059 078 A1 | 6/2009 |
| DE | 299 07 573 U1 | 9/2009 |
| EP | 1 099 470 A1 | 5/2001 |
| JP | S425302 Y1 | 3/1967 |
| JP | S4872753 A | 10/1973 |
| JP | 2002537090 A | 11/2002 |
| JP | 2005270955 A | 10/2005 |
| JP | 2006263727 A | 10/2006 |
| JP | 2007527283 A | 9/2007 |
| JP | 2009509758 A | 3/2009 |
| JP | 2009195407 A | 9/2009 |
| JP | 2011521670 A | 7/2011 |
| RU | 29673 U1 | 5/2003 |
| RU | 2264250 C2 | 11/2005 |
| SU | 1058590 A | 12/1983 |
| SU | 1668154 A1 | 8/1991 |
| WO | 98/43727 A1 | 10/1998 |
| WO | 2005-082549 A2 | 9/2005 |
| WO | 2007-041878 A1 | 4/2007 |

OTHER PUBLICATIONS

Written Opinion for International Patent Application No. PCT/EP2012/052201 mailed on Apr. 26, 2012.

* cited by examiner

DYNAMIC MIXER

PRIORITY CLAIM

The present application is a National Stage of International Application No. PCT/EP2012/052201, filed on Feb. 9, 2012, which claims priority to European Patent Application No. 11156133.8 filed on Feb. 28, 2011, the entire contents of which are being incorporated herein by reference.

The invention relates to a dynamic mixer.

A dynamic mixer is known from WO 2007/041878 A1 for mixing components having different volume proportions, in particular for manufacturing dental impression materials. An antechamber is arranged in the inner space of the mixer housing within which the mixing rotor has a distributor body for distributing the components about its axis of rotation in order thereby to achieve a correct mixing ratio between the components and to avoid air inclusions. Subsequently, the premixed components move into a main chamber through at least one passage opening for their complete mixing.

In particular with high mixing ratios of viscous or pasty components, it is particularly difficult to keep the correct mixing ratio constant and to maintain a good mixing. The mixing generally takes place by shear forces, with the components being urged through the mixer. The mixer has a housing and a rotor element which is rotatably arranged in the housing, whereby the housing has one respective inlet opening for at least two components and at least one outlet opening. A ring-shaped intermediate space is provided between the rotor element and the housing in which a mixing element attached to the rotor element is arranged. The rotor element comprises the body element and the mixing element. This mixing element is formed as a vane element which projects away from the body element into the intermediate space. A plurality of such vane elements are preferably present. In addition, static mixing elements can also project from the inner wall of the housing into the intermediate space, which can, however, only be realized with difficulty from a technical manufacturing aspect. The components are rearranged by the vane element or elements and by the static mixing elements, which may additionally be present, a multiple of tines in a kneading manner. The aim is to produce a phase boundary area between the components which is as large as possible in that a plurality of layers which are as fine as possible are produced by dividing and rearranging the flowing components to achieve a mixing effect. This mixing effect was until now produced using mixing elements by means of which the flows are split as a consequence of the movement of the rotor element transversely to the main direction of flow and some of the filler compound is predominantly urged away against the main direction of flow so that inflowing filler compound flows in behind the mixing element and a rearrangement and layer formation of the components in the filler compound is achieved in this manner. Difficult mixing tasks result in longer mixers, a larger force expenditure and thus increased energy consumption for the mixer drive and in greater resistance to urge the components through the mixer.

The following disadvantageous consequences therefore previously had to be coped with: a longer mixer, an increased energy consumption and also an increased pressure loss. Accordingly, larger and heavier drive units and batteries for the discharge device have to be provided, which restricts the handling for the application of the mixture, increases the energy requirement and reduces the use times of the discharge device in the case of battery operation.

Since the components react with one another and harden in the mixer on an interruption of the discharge, the mixer must be replaced and disposed of after use and together with the components contained therein.

The document WO2005/082549 A2 shows a dynamic mixer which has mixing elements, which are arranged along the rotor hub and protrude into the mixing space. The mixing elements have a triangular, rectangular or trapezoidal cross-section. The tip of the triangle or the shorter side of the two parallel sides of the trapezoid are exposed to fluid flow. As disclosed in the document WO2007/041878 A1 in particular for mixing elements of triangular or trapezoidal cross-section, a portion of the filler mass is deflected mostly against the main direction of flow, that means in the direction of the mixer inlet, such that subsequently inflowing filler mass reaches the mixing element and thereby a relocation and layer formation of the components of the filler mass is obtained which leads to the same disadvantages as already described in WO2007/041878 A1.

The document DE 102 42 100 A1 shows a stirrer mixer which is disposed with a stirrer being arranged rotatably around a central axis. The stirrer is configured as an inclined blade stirrer. The sense of rotation of the stirrer is chosen such that the stirrer conveys the filler mass in the direction of the mixing outlet, such that an axial pumping effect occurs, which has the consequence that the mixing chamber pressure is lowered with increasing stirrer rotary speed or held constant. An increased conveying effect as well as a smaller pressure drop can be obtained with this stirrer mixer, however it has the consequence that the mixing effect is decreased for a single inclined blade stirrer element. For this reason the overall mixer length is increased, such that this solution is not suitable to create a mixer of a mixing length which is as small as possible.

The document WO98/43727 A1 shows a dynamic mixer with mixing elements which are of a rhomboid or cylindrical shape. A mixing passage is formed between the rotor hub and the mixer housing, the diameter of which decreases in direction of the discharge end of the mixer. Thereby an acceleration of the axial movement of the filler mass is achieved, that means that the filler mass flows through the mixer faster, however the mixing quality is increased only by means of additional measures, namely in that the mixing wings are arranged in a different direction in different axial zones of the mixer shaft which results in an increase of the pressure drop. A similar solution is also shown in FIG. 6, 7 of DE 199 47 331 A1, with the substantial difference that the mixer housing is rotatable relative to the mixer hub. In order to achieve a sufficient mixing of filler masses of a higher viscosity with this solution, the mixer wings are arranged in a greater plurality of planes which has the consequence of an increased axial length of the mixer.

The document DE 101 12 904 A1 shows a dynamic mixer which has a retention chamber, such that the component with the higher volume portion enters the mixing chamber in a delay with respect of the component with the small volume portion. Hereby it is safeguarded, that both components are mixed through from the start, thereby the mixer length can be decreased. However it has to be taken care that no dead zones are created. The wing elements should not show a conveying effect. Therefore no improvement of the mixing quality with respect to WO2007/041878 A1 is achievable.

The document DE 10 2007 059 078 A1 shows a dynamic mixer which has trapezoidal wing elements and apertured plates as intermediate elements. The arrangement is used to decrease the speed of rotation of the media in the mixer, what can be disadvantageous for component mixtures hardening quickly. A conveying effect of any kind is not wanted by this arrangement as the opposite effect is desired.

The document US2009/0034357 A1 shows a dynamic mixer with a deflection element, which is arranged in a discharge end of the rotor hub. The mixing elements of US2009/0034357 A1 substantially correspond to DE 101 12 904 A1. This document thus shows that the mixing effect of the wing elements is not considered sufficient and therefore an additional element, namely the deflection element is to be foreseen to increase the mixing quality. Alternatively a static mixer can be foreseen for this purpose on the discharge end of the mixer as shown in the document US2009/0034357 A1. The wing elements of trapezoidal cross-section have been shown already in WO2005/082549 A2.

According to document EP 1 099 470 A1, fixed peeling elements are arranged at the mixer housing between the wing elements arranged rotatably at the rotor hub. These peeling elements do not have a conveying effect, but serve the improvement of the mixing.

The document DE 199 47 331 A1 shows a dynamic mixer with a bearing of the rotor hub in the mixer discharge end. The rotor hub is disposed with a passage for the discharge of the mixture due to the fact that the rotor hub is supported in the mixer discharge end. The mixing wings appear not to have any conveying effect, as in column 3, line 48 of this document, it is pointed out that the pistons press the filler mass outwardly. These pistons appear to belong to a plunger of a dispensing unit, by which the contents of the cartridge is expelled.

It is therefore the object of the invention to find a mixer for difficult mixing tasks which is short and manages with as little energy effort for the rotor element as possible as well as with a smaller pressure loss through the mixer. The mixers are produced in high volumes. Material for the mixer, for the components and also costs for the disposal of the used mixers can be saved with small mixers.

The object of the invention is satisfied by a dynamic mixer for a plurality of fluid components which has a housing and a rotor element which is rotatably arranged in the housing. The housing has an inlet opening for at least one respective component and at least one outlet opening, with a ring-shaped intermediate space being provided between the rotor element and the housing in which a mixing element connected to the rotor element is arranged. The mixing element has a vane element which is formed as a directing element for conveying the components from the inlet opening to the outlet opening. The vane element has a directing element and a directing surface which has a concave curvature with respect to the outlet opening and is further remote from the outlet opening at the onflow side 70 than at the outflow side 71.

In accordance with a further embodiment, the vane element does not cover more than 50% of a plane laid through the intermediate space, said plane containing the vane element and being aligned normal to the axis of the dynamic mixer. A plurality of vane elements can be arranged in at least two parallel planes substantially perpendicular to the axis of the dynamic mixer.

In accordance with an embodiment, a first vane element and a second vane element downstream of the first vane element are arranged in a main chamber, with the shortest spacing between the first vane element and the second vane element amounting to at least one third of the spacing between the rotor element and the boundary of the main chamber given by the housing. The shortest distance is thereby defined as the distance between the delimitation of the main chamber in the housing and the vane element in direction of the longitudinal axis of the dynamic mixer.

In accordance with an embodiment, the vane element has a substantially trapezoidal cross-sectional surface. The vane elements can in particular have a dam surface at the onflow side 70, with the plane of the dam surface being arranged parallel to the axis of the rotor element or at an angle such that the dam surface faces in the direction of the outlet opening.

The vane elements of the dynamic mixer can be arranged in particular pair wise. A pair wise arrangement means in this case that two vane elements are arranged in a plane which is normal to the rotor axis. The vane elements can in particular be arranged opposite to each other in a pair wise arrangement. That means that a first vane element can be arranged in a staggered manner in an angle of 180 degrees to a second vane element of a pair of vane elements. For neighboring pairs of vane elements the following relation holds. The vane element of the first pair is rotated with respect of the vane element of the second pair by a rotation of an angle, whereby the second pair is moved relative to the first pair in the direction of the outlet or against the direction of the outlet along the rotor axis. The geometrical configuration of two neighboring pairs of vane elements is such that the first pair of vane elements can be transformed into the second pair of vane elements by an axial movement along the rotor axis and a subsequent rotation about an angle of 90 degrees.

Neighboring pairs of vane elements can have a different geometrical configuration. In particular, neighboring pairs of vane elements can have a geometrical configuration which is either conveying or not conveying. By "conveying" it is in particular meant that the inclination and curvature of at least one directing surface of the vane element favors an inflow of filling mass arranged upstream and contributes to the mixing thereof.

In accordance with an embodiment, the housing of the dynamic mixer has a first housing part and a second housing part, with the first housing part containing the inlet openings and the second housing part containing the outlet opening. In accordance with an embodiment, the rotor element is supported in a housing part.

According to an embodiment, the vane element has a dam surface on the onflow side 70 and an end surface on the outflow side 71, and a peripheral surface 72 extending at the outer periphery between the dam surface on the onflow side 70 and the end surface on the outflow side 71, a base surface 73, which faces the inlet openings and cover surface 74 which faces the outlet opening.

In particular, the peripheral surface 72 can have a base edge 75 facing the inlet openings which has a continuous curvature. The radius of curvature increases according to an embodiment from the base edge 75 of the dam surface on the onflow side 70 to the end surface on the outflow side 71. Alternatively or in combination thereto, the base edge 75 can have s-shaped extent. In particular the radius of curvature of the base edge 75 from the onflow side 70 to the outflow side 71 can be constant at least for sections. Alternatively or in addition thereto, the peripheral surface 72 can have a cover edge 76 facing the outlet opening which has a continuous curvature. The extent of curvature of the cover edge 76 can differ from the extent of curvature of the base edge 75.

The curvature can have a minimal radius of curvature of 1 mm and a maximal radius of curvature of 100 mm, preferably a maximal radius of curvature of up to 50 mm.

Preferably the mixer contains maximal 5 rows of vane elements, preferably maximal 4 rows of vane elements, particularly preferred maximal 3 rows of vane elements, which are arranged on the rotor element. Thereby the overall construction length of the mixer is substantially reduced with respect to the prior art. Therefrom results not only a decrease of the manufacturing costs but also a decrease of the filling volume, thereby the filler mass remaining in the passage after use of the mixer is reduced. Thereby the waste of filler mass can be reduced with a mixer according to one of the embodiments of the invention.

The housing includes, in accordance with an embodiment, a first antechamber and a main chamber, with the inlet openings opening into the first antechamber in which the components are led together for the first time. A second antechamber can in particular be provided between the first antechamber and the main chamber. At least one opening between the rotor element and the housing for the passage of the components can be arranged between the first antechamber and the second antechamber. A mixing element can be arranged in at least one of the first and second antechambers in accordance with an embodiment. The components can be guided radially in the direction of the rotor element in the second antechamber and can be guided by the mixing elements attached at the housing side or at the rotor element before they are guided into the main chamber after a deflection in the axial direction.

In accordance with an embodiment, the first housing part has an apparatus for piercing a container containing the components in at least one of the inlet openings.

It has been shown that, contrary to the general opinion of the prior art, good results are also achieved with respect to rearrangement and layer formation when the filler compound is urged in the direction of the outlet opening at least by individual mixing elements at least in the proximity of these mixing elements not against, but in the direction of the main direction of flow and filler compound located downstream is pulled in behind it from the more slowly flowing main flow. The main flow is located between the inner wall of the housing and the rotor element. The geometry of the mixing elements influences the flow substantially only locally, but influences the mixing effect, the rotary resistance of the rotor element and the pressure loss of the components through the mixer. At least some of these mixing elements accordingly have a conveying effect which reduces the resistance for the urging through of the components and the force expenditure for the rotor drive. It was also shown that the dwell time of the components in the dynamic mixer can be reduced for a required mixing effect and the dynamic mixer can thus be constructed more compactly overall and with less content.

The mixing ratio of the first and second components can amount to 1:1, but can also lie at 1:10 to 1:50 or even higher.

The use of the dynamic mixer preferably takes place in autonomous hand discharge units or in stationary desktop units.

The invention will be explained in the following with reference to the drawings. There are shown.

Figure 1:
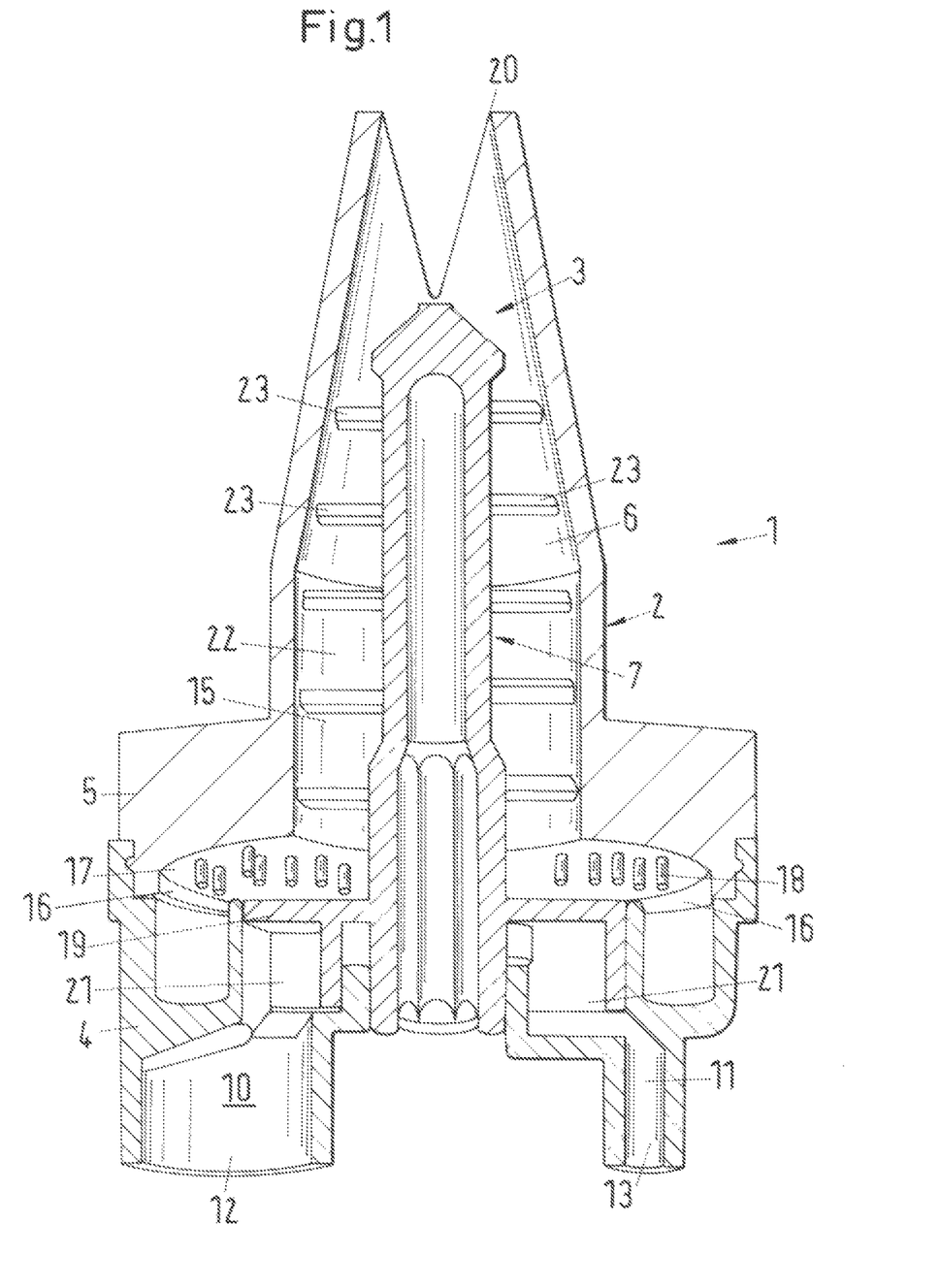
FIG. 1 a section through a dynamic mixer in accordance with a first embodiment of the invention, FIG. 2 a section through a dynamic mixer in accordance with a second embodiment of the invention, FIG. 3 a view of a rotor element for a dynamic mixer, FIG. 4 a view of a rotor end in accordance with a first variant in accordance with the invention, FIG. 5 a view of a rotor end in accordance with a second variant in accordance with the invention, FIG. 6 a view of a rotor end in accordance with a third variant in accordance with the invention, FIG. 7 a view of a rotor end in accordance with the first variant in accordance with the invention identifying dimensional references of vane elements.

FIG. 1 shows a dynamic mixer for a plurality of fluid components. The dynamic mixer 1 has a housing 2 and a rotor element 3 which is arranged rotatably about a rotor axis 8 in the housing 2. In the present embodiment, the housing 2 is made in two parts; it contains a first housing part 4 in which the inflow of the components is located and a second housing part 5 which serves for the production of a mixture from the plurality of fluid components. The first housing part 3 is connected to the second housing part via a latch connection, a snap-in connection or a weld connection as soon as the rotor element 3 is received in the second housing 5. The first housing part 4 has an inlet opening 12, 13 for at least one respective component. The inlet openings 12, 13 can have different diameters which are dependent on the desired mixing ratio of the components. The inlet openings open into corresponding inlet passages 10, 11 which are arranged in the first housing part 4. The inlet passages 10,11 open into a first antechamber 21 which is provided with outlet openings 16 which are designed substantially as an outer ring gap and which open into an inner space 15 of the second housing part 5.

The second housing part 5 has at least one outlet opening 20. The mixture of the components exits the dynamic mixer through the second outlet opening 20. The outlet opening 20 can be especially designed in accordance with the intended use. In the present case, a V-shaped incision is provided. The form of a triangular bead results on the discharge of the filler compound with the help of this V-shaped incision. The inner space 15 of the second housing part 5 serves for the reception of the rotor element 3.

The inner space 15 has a second antechamber 17 and a main chamber 22. The components which have been brought into contact with one another for the first time and premixed in the first antechamber 21 come into the second antechamber 13. The components are directed from the second antechamber 17 to the main chamber 22. A further mixing can take place in the second antechamber 17. A plurality of mixing elements 18 are arranged in the antechamber for this purpose. These mixing elements are designed as pin elements which project into the antechamber. The pin elements can alternatively be arranged on a rotary surface 19 of the rotor element 3 or, as shown in FIG. 1, can project from the inner wall of the housing bounding the antechamber into the antechamber 17. Shear forces are exerted onto the components by the rotary surface 19 and the pin elements 18. The components are hereby admixed with one another in a relatively finely spaced manner.

A ring-shaped intermediate space which forms the main chamber 22 in which a mixing element 7 connected to the rotor element 3 is arranged is provided between the rotor element 3 and the inner wall 6 of the housing.

The mixing element 7 includes a plurality of vane elements 23 in the main chamber 22. The vane elements 23 protrude as projections into the main chamber 22. The final complete mixing of the components takes place in this main chamber 22 in that the components are taken up by the vane elements and are rearranged. At least some of the vane elements can be formed as a directing element for conveying the components through the inner space 15 in the direction of the outlet opening 20.

Figure 2:
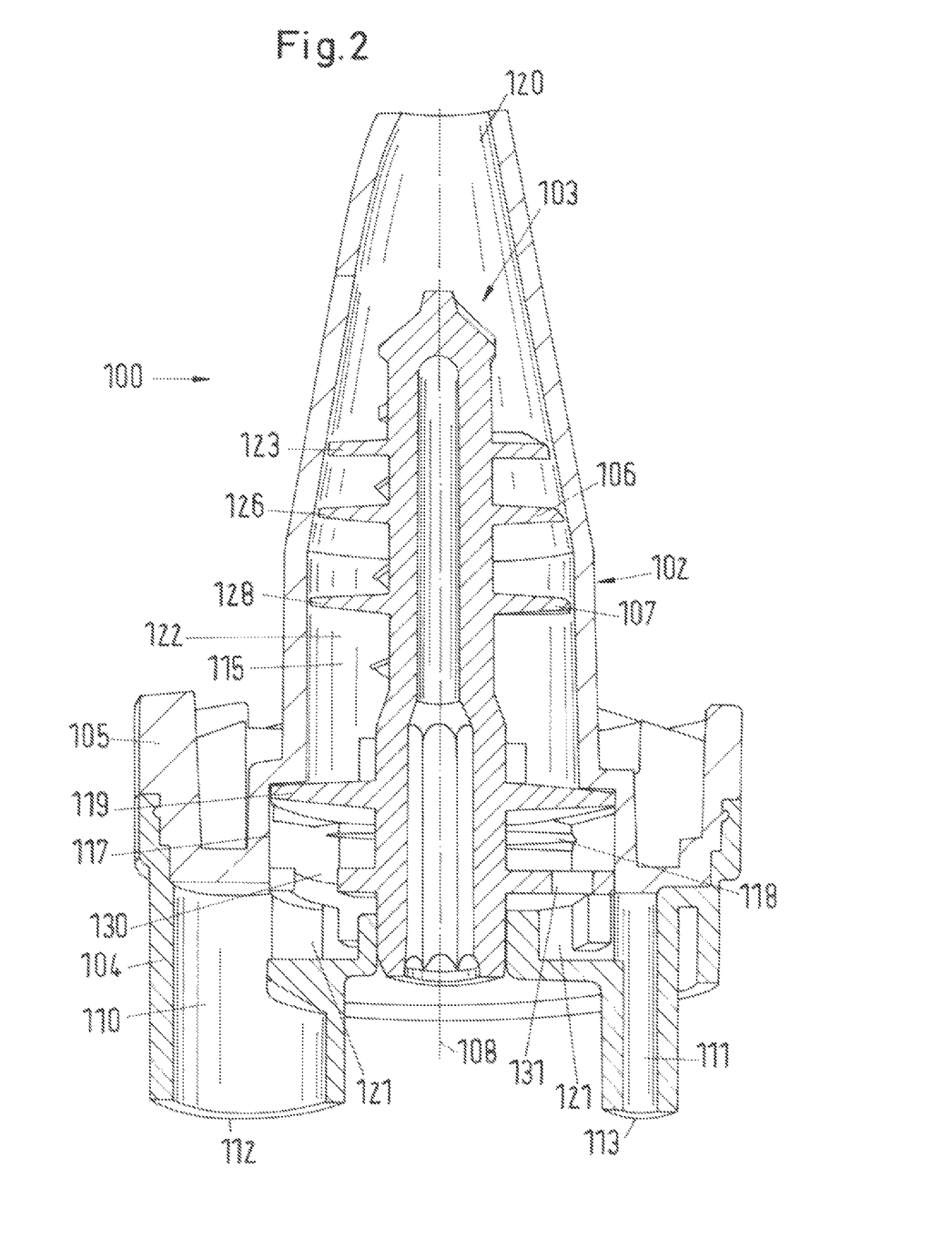

FIG. 2 shows a section through a dynamic mixer in accordance with a second embodiment of the invention for the mixing of a plurality of fluid components. The dynamic mixer 100 has a housing 102 and a rotor element 103 which is arranged rotatably about a rotor axis 108 in the housing 102. In the present embodiment, the housing 102 is made in two parts; it contains a first housing part 104 in which the inflow of the components is located and a second housing part 105 which serves for the production of a mixture from the plurality of fluid components. The first housing part is connected to the second housing part via a latch connection, a snap-in connection or a weld connection as soon as the rotor element 103 is received in the second housing 105. The first housing part 104 has an inlet opening 112, 113 for at least one respective component. The inlet openings 112, 113 can have different diameters which are dependent on the desired mixing ratio of the components. The inlet openings open into corresponding inlet passages 110, 111 which are arranged in the first housing part 104. The inlet passages 110 open into a first antechamber 121 which is provided with outlet openings 130 which open into an inner space 15 of the second housing part 105.

The second housing part 105 has at least one outlet opening 120. The mixture of the components exits the dynamic mixer through the outlet opening 120. The inner space 115 of the second housing part 105 serves for the reception of the rotor element 103.

The inner space 115 includes a second antechamber 117 and a main chamber 122. The components which have been brought into contact with one another for the first time and premixed in the first antechamber 121 come into the second antechamber 117. The components are directed from the second antechamber 117 to the main chamber 122. A further premixing can take place in the second antechamber 117. A mixing element 118 is arranged in the second antechamber 117 for this purpose. The mixing element 118 is formed as a vane element which is connected to the rotor element 103. In addition, further vane elements 118 can be arranged on a rotary surface 119 of the rotor element 103, which is not shown in FIG. 2. Shear forces are exerted onto the components by the rotary surface 119 and the pin elements 118. The components are hereby admixed with one another.

A ring-shaped intermediate space in which a mixing element 107 connected to the rotor element 103 is arranged is provided between the rotor element 103 and the inner wall of the housing.

The mixing element 107 includes a plurality of vane elements 123 in the main chamber 122. The vane elements 123 protrude as projections into the inner space 115 which forms the main chamber 122. The complete mixing of the components takes place in this main chamber in that the components are taken up by the vane elements and are rearranged. At least some of the vane elements can be formed as a directing element for conveying the components through the inner space 115 in the direction of the outlet opening 120. The vane elements can in particular be formed in accordance with each of the embodiments shown in FIGS. 4 to 6.

It is also not necessary that adjacent vane elements arranged behind one another with respect to the rotor axis 108 have the same spacing from one another. The spacing of the vane element 123 arranged closest to the outlet opening 120 from the vane element 126 is, for example, smaller than the spacing of the vane elements 126 from the vane element 128.

Figure 3:
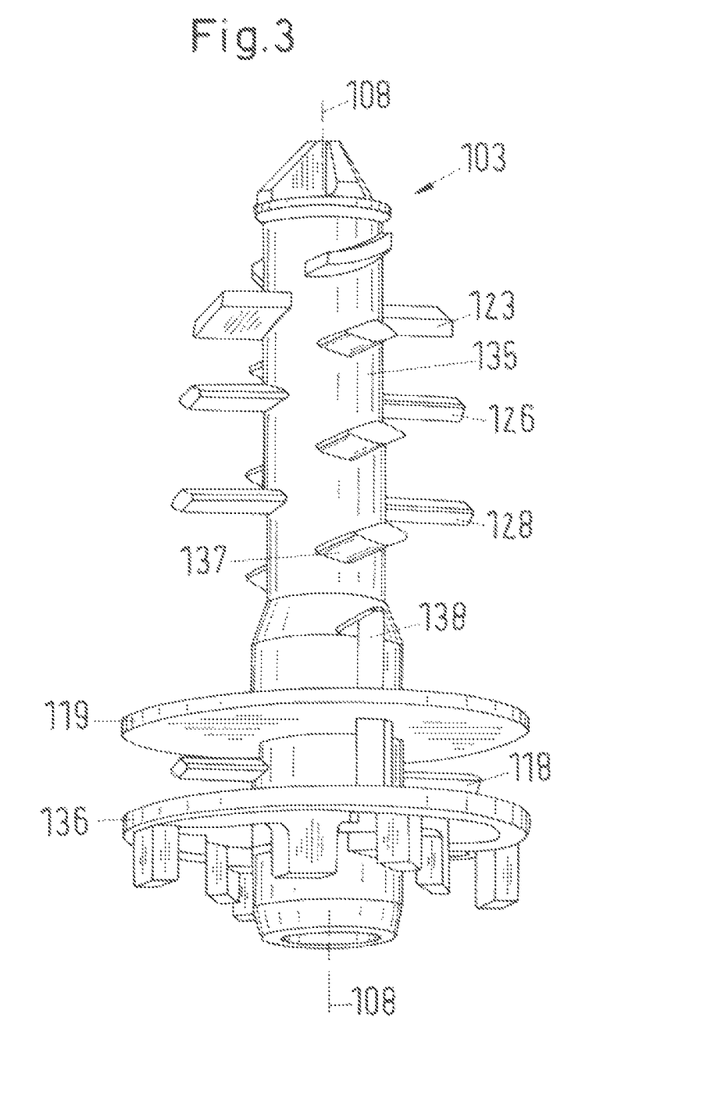

FIG. 3 shows a view of a rotor element for use in one of the dynamic mixers in accordance with one of the preceding embodiments. The rotor element corresponds to the rotor element 102 shown in FIG. 2 so that the same reference numerals as in FIG. 2 are used for the same parts. However, this reference is not to be understood as a restriction such that the rotor element can only be used in connection with the embodiment in accordance with FIG. 2. It is rather the case that the rotor element can likewise be used in a housing in accordance with any one of the other embodiments with a slight adaptation of the geometry of the housing. The rotor element 103 has a rotor axis 108 along which a rotor element hub 135 is arranged. The rotor element hub 135 carries an annulus element 136 which contains the outlet openings 130, 131. The components supplied into the first antechamber 121 from the inlet passages 110, 111 (see FIG. 2) enter into the second antechamber 117 through these outlet openings 130, 131. The annulus element 136 represents a boundary of the first antechamber 121. Directing elements which project into the first antechamber 121 are attached to the annulus element 136. The outer directing elements attached to the annulus element 136 shear the components from the outlet openings of the inlet passages 110, 111 and guide them into the space of the first antechamber 121 and effect a first bringing into contact of the components and secure the keeping constant of the mixing ratio. Further inwardly disposed directing elements produce a first premixing. A second boundary of the second antechamber 117 is the rotary surface 119 which is attached downstream of the annulus element 136 on the rotor element hub 135. At the peripheral side, the antechamber 117 is bounded by the second housing part 105 (see FIG. 2).

The components are premixed by a mixing element 118 which is arranged in the antechamber on the rotor element hub 135 and as needs be at the rotary surface 119 or at the annulus element 136 at the downstream side. The mixing element can be formed as a vane element in accordance with any one of the embodiments in accordance with FIGS. 4 to 6.

To move into the main chamber 122 (see FIG. 2), the components flow about the rotary surface 119. A narrow ring-shaped gap or ring shaped gap segments through which the components enter and move into the main chamber via supply passages shaped at the housing side remains between the rotary surface 119 and the inner wall of the second housing part. Furthermore, vane elements 123, 126, 128 which are formed as directing elements are arranged in the main chamber downstream of the rotary surface 119. In addition, vane elements 137 can be provided which are formed in diamond shape as described, for example, in WO98/43727. Furthermore, an arcuate vane element 138 is shown which is directly adjacent the rotary surface 119 and shears away the filler compound from the inlet openings and directs it into the main chamber. Similar vane elements can also be arranged further downstream and effect a scraping of the filler compound from the wall of the main chamber 22, 122.

Vane elements of the same type are preferably arranged opposite one another at the same height, with the height being measured along the rotor axis 108.

Figure 4:
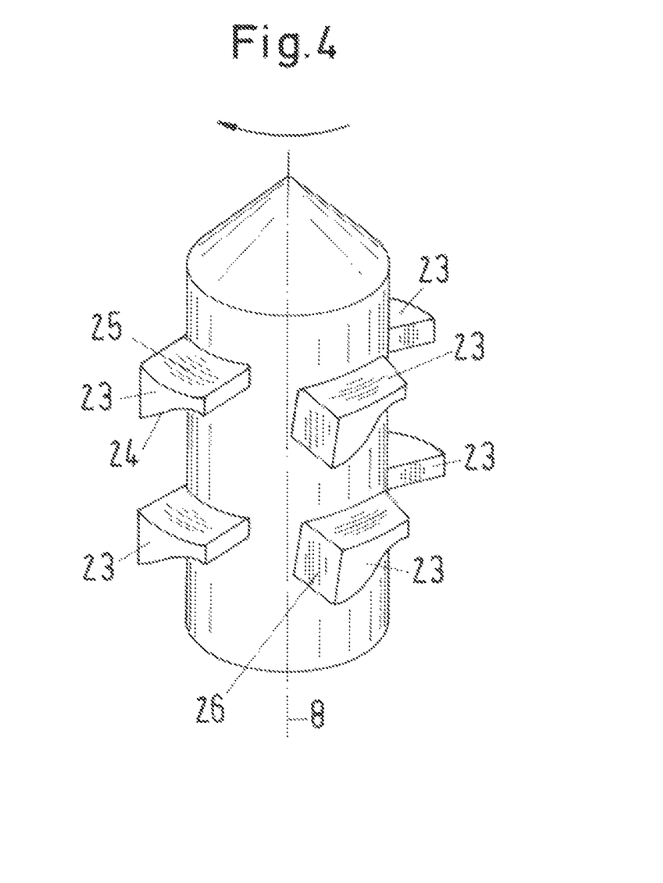

FIG. 4 shows a view of a rotor end of the rotor element 3, 103 in accordance with a first variant in accordance with the invention which shows vane elements 23 which are formed as a directing element. The directing element in accordance with this embodiment has a first directing surface 24 which is aligned in the direction of the first antechamber 17 and a second directing surface 25 which is aligned in the direction of the outlet opening 20. The second directing surface 25 extends substantially parallel to a normal plane on the rotor axis 8, whereas the first directing surface is formed such that the cross-sectional surface of the directing element increases in the direction of rotation. The onflow surface of the dam surface 26 of the vane element is advantageously inclined away from the plane of the axis of rotation such that it faces in the direction of the outlet opening 20.

Figure 5:
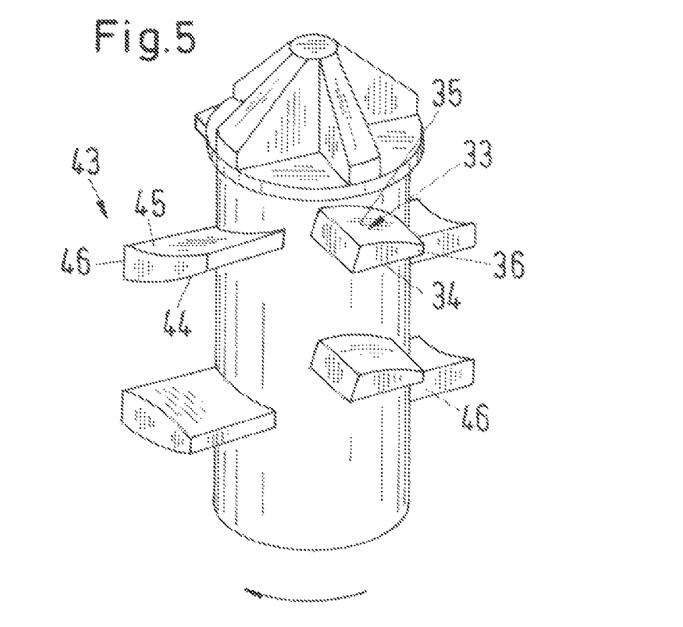

FIG. 5 is a view of a rotor end of a rotor element 3, 103 in accordance with a second variant in accordance with the invention which contains directing elements of different construction. The vane element 33 has a first directing surface 34 which is aligned in the direction of the second antechamber 17, 117 and a second directing surface 35 which is directed in the direction of the outlet opening 20, 120. The second directing surface 35 has a convex curvature. The normal spacing between the first directing surface and the second directing surface increases in the direction of rotation. The rear end of the first and second directing surfaces can in particular be formed as an edge 36. An onflow surface which is preferably inclined relative to the rotor axis, at which the filler compound flowing in onto the directing element is distributed and which is urged in the direction of the outlet opening 20, 120 is located opposite the edge 36. The inclination and curvature of the directing surface 35 promotes a subsequent flow of filler compound above it and thus contributes to its mixing.

The vane element 43 has a first directing surface 44 which is aligned in the direction of the second antechamber 17, 117 and a second directing surface 45 which is directed in the direction of the outlet opening 20, 120. The second directing surface 45 has a curvature. The normal spacing between the first directing surface 44 and the second directing surface 45 can increase, decrease or remain the same in the direction of rotation. The front ends of the first and second directing surfaces 44, 45 are arranged at a spacing from one another. A dam surface 46 is hereby formed which as a disturbance element deflects and divides the filler compound composed of the components. The portion of the filler compound which is directed over the second directing surface 45 is conveyed by its curvature in the direction of the outlet opening 20, 120. The first directing surface 44 can also have a curvature. The curvatures of the first and second directing surfaces 44, 45 can in particular be the same.

Figure 6:
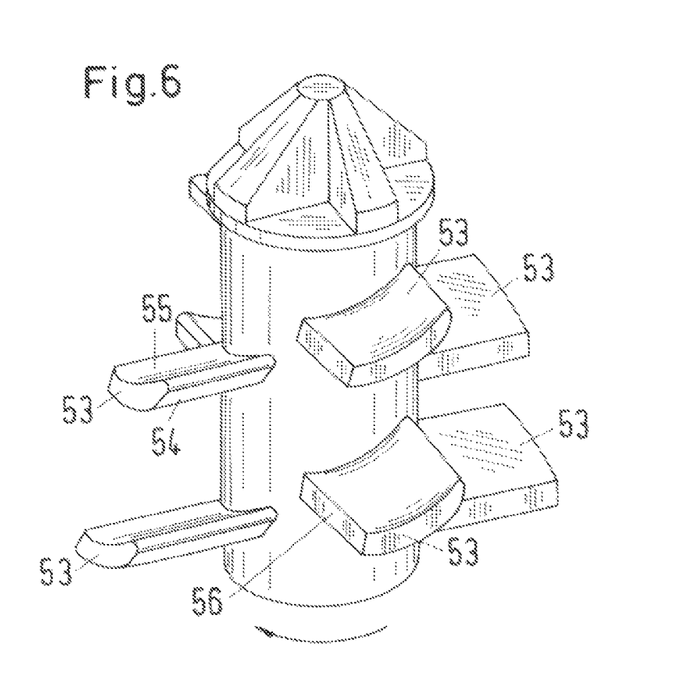
Figure 7:
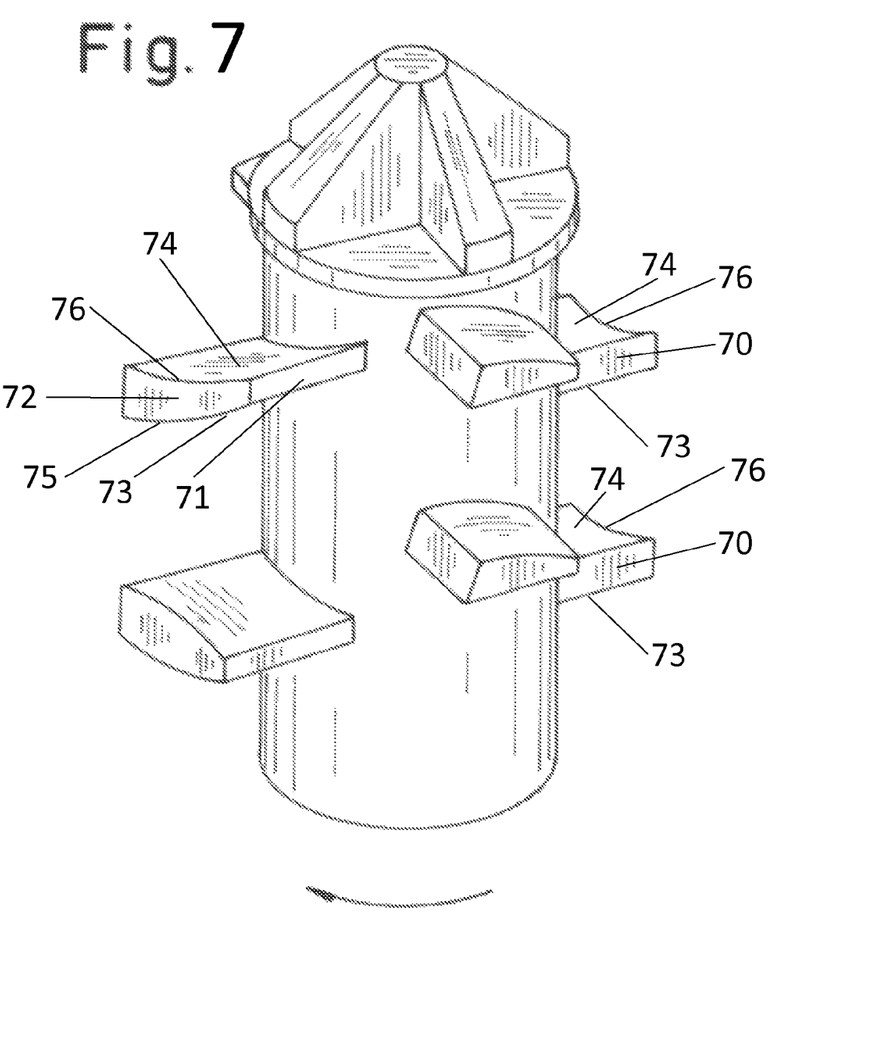

A vane element 53 can in particular be provided in accordance with FIG. 6 which has an alignment in the direction of the outlet opening 20, 120. That is, the first directing surface 54 has a convex curvature. The second directing surface 55 has a concave surface with respect to the outlet opening. The geometrical design of the vane element can be similar to the vane element 43. A rotor element can in particular be composed only of vane elements 53.

A plurality of vane elements are preferably arranged at the periphery of the rotor element in accordance with every embodiment. A plurality of vane elements can in particular also be arranged behind one another in the direction of the axis of the rotor element. It is advantageous from a technical manufacturing aspect if diametrically opposite vane elements are of the same type. The vane elements arranged behind one another are preferably not all of the same type.

The invention claimed is:

1. A dynamic mixer for a plurality of fluid components, comprising:
    a housing including a first inlet opening for a first component of the plurality of fluid components, a second inlet opening for a second component of the plurality of fluid components, at least one outlet opening, a first antechamber, a second antechamber, a main chamber, the first and second inlet openings are configured to communicate with first and second sources for the first and second components, respectively, and configured to keep the components separate until they are mixed in the first antechamber;
    a rotor element having a rotor axis that defines an axis of the dynamic mixer, the rotor element being rotatably arranged in the housing so as to define a ring-shaped intermediate space between the rotor element and the housing, the first inlet opening being connected to the first antechamber by a first inlet passage, the second inlet opening being connected to the first antechamber by a second inlet passage, the first and second inlet passages extending along a longitudinal length that is parallel to the rotor axis;
    a mixing element connected to the rotor element and arranged in the ring-shaped intermediate space, the mixing element including a vane element including a first directing surface and being formed as a directing element configured to convey the components from the inlet opening to the outlet opening,
    the first directing surface having a concave curvature with respect to the outlet opening, and is further remote from the outlet opening at an onflow side than at an outflow side, and the second antechamber being disposed between the first antechamber and the main chamber, and the first antechamber being arranged to receive the components before the second antechamber and the main chamber.

2. The dynamic mixer in accordance with claim 1, wherein
    the vane element covers 50% or less of a plane laid through the intermediate space, the plane containing the vane element and being aligned normal to the axis of the dynamic mixer.

3. The dynamic mixer in accordance with claim 1, wherein
    the vane element is one of a plurality of vane elements, the plurality of vane elements being arranged in a plurality of rows substantially perpendicular to the axis of the dynamic mixer.

4. The dynamic mixer in accordance with claim 3, wherein
    the plurality of vane elements further includes a first vane element and a second vane element disposed downstream of the first vane element, the first and second vane elements being arranged in the main chamber,
    the first vane element being spaced from the second vane element, a spacing between the first vane element and the second vane element amounting to at least one third of a spacing between the rotor element and a boundary of the main chamber, and
    the boundary of the main chamber being defined by the housing, the spacing between the first and second vane elements being measured in the direction of the axis of the dynamic mixer.

5. The dynamic mixer in accordance with claim 3, wherein
    the vane elements have a dam surface, and
    a plane of the dam surface is arranged parallel to the axis of the rotor element or at an angle such that the dam surface faces toward the outlet opening.

6. The dynamic mixer in accordance with claim 1, wherein
    the housing has a first housing part and a second housing part,
    the first housing part containing the first and second inlet openings and the second housing part containing the outlet opening.

7. The dynamic mixer in accordance with claim 5, wherein
the first directing surface is a base surface facing the first and second inlet openings,
the vane element further includes
a dam surface on the onflow side,
an end surface on the outflow side,
a peripheral surface extending on an outer periphery of the vane element between the dam surface on the onflow side and the end surface on the outflow side,
a cover surface facing the outlet opening.

8. The dynamic mixer in accordance with claim 7, wherein
the peripheral surface has a base edge facing the first and second inlet openings, the base edge having continuous curvature.

9. The dynamic mixer in accordance with claim 8, wherein
a radius of curvature of the base edge increases from the dam surface on the onflow side to the end surface on the outflow side.

10. The dynamic mixer in accordance with claim 8, wherein
the base edge has an s-shaped extent.

11. The dynamic mixer in accordance with claim 8, wherein
a radius of the curvature of the base edge is constant at least for sections from the onflow side to the outflow side.

12. The dynamic mixer in accordance with claim 7, wherein
the peripheral surface has a cover edge facing the outlet opening,
the cover edge having a continuous curvature.

13. The dynamic mixer in accordance with claim 7, wherein
an extent of the curvature of the cover edge differs from an extent of curvature of the base edge.

14. The dynamic mixer in accordance with claim 8, wherein
the curvature of the base edge has a minimal radius of curvature of 1 mm and a maximal radius of curvature of 100 mm.

15. The dynamic mixer in accordance with claim 1, wherein
a maximum of 5 rows of vane elements are arranged on the rotor element.

16. The dynamic mixer in accordance with claim 1, wherein
a maximum of 4 rows of vane elements are arranged on the rotor element.

17. The dynamic mixer in accordance with claim 1, wherein
a maximum of 3 rows of vane elements are arranged on the rotor element.

18. A dynamic mixer for a plurality of fluid components comprising:
a housing including a first inlet opening for a first component of the plurality of fluid components, a second inlet opening for a second component of the plurality of fluid components, a first antechamber, a second antechamber, a main chamber, an outlet opening, the first and second inlet openings are configured to communicate with first and second sources for the first and second components, respectively, and configured to keep the components separate until they are mixed in the first antechamber;
a rotor element having a rotor axis that defines an axis of the dynamic mixer, the rotor element being rotatably arranged in the housing to rotate in a rotational direction, the first inlet opening being connected to the first antechamber by a first inlet passage, the second inlet opening being connected to the first antechamber by a second inlet passage, the first and second inlet passages extending along a longitudinal length that is parallel to the rotor axis; and
a mixing element extending from the rotor element towards the housing, the mixing element having a vane element formed to convey the fluid components from the inlet opening to the outlet opening, the vane element having a first directing surface and a second directing surface,
the first directing surface having a concave curvature when viewed from the outlet opening, the concave curvature being farther from the outlet opening at an onflow side than at an outflow side, and
the second directing surface having a curvature different from the first directing surface with respect to the outlet opening, and being disposed on an opposite side of the directing element from the first directing surface.

* * * * *